(12) United States Patent
Schneider (10) Patent No.: US 7,966,917 B2
(45) Date of Patent: Jun. 28, 2011

(54) MICROTOME HAVING A LEVER ARRANGEMENT

(75) Inventor: Volker Schneider, Sinsheim-Weiler (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 123 days.

(21) Appl. No.: 11/781,386

(22) Filed: Jul. 23, 2007

(65) Prior Publication Data

US 2008/0022823 A1    Jan. 31, 2008

(30) Foreign Application Priority Data

Jul. 25, 2006 (DE) .......................... 10 2006 034 879

(51) Int. Cl.
*B26D 1/00* (2006.01)
(52) U.S. Cl. ........................................ 83/651; 83/915.5
(58) Field of Classification Search .............. 83/651, 83/915.5; 74/20, 21, 490.14, 497, 519, 523
See application file for complete search history.

(56) References Cited

U.S. PATENT DOCUMENTS

| | | | | |
|---|---|---|---|---|
| 546,626 A | * | 9/1895 | Sheanfeld | 74/21 |
| 4,141,258 A | * | 2/1979 | Walzer | 74/540 |
| 4,269,092 A | * | 5/1981 | Disharoon | 83/42 |
| 4,505,175 A | * | 3/1985 | Reichel | 83/703 |
| 4,625,608 A | * | 12/1986 | Behme et al. | 83/713 |
| 4,691,151 A | * | 9/1987 | Behme et al. | 318/571 |
| 4,754,675 A | * | 7/1988 | Segal | 83/437.4 |
| 4,926,707 A | * | 5/1990 | Yamada | 74/96 |
| 4,967,629 A | * | 11/1990 | Behme | 83/714 |
| 5,048,300 A | * | 9/1991 | Lihl | 62/48.1 |
| 5,522,294 A | * | 6/1996 | Krumdieck | 83/411.1 |
| 5,752,425 A | * | 5/1998 | Asakura et al. | 83/713 |
| 5,761,977 A | * | 6/1998 | Jakobi et al. | 83/13 |
| 5,782,572 A | * | 7/1998 | Thiem | 403/90 |
| 7,044,038 B2 | * | 5/2006 | Hess | 83/57 |
| 7,313,993 B2 | * | 1/2008 | Foerderer | 83/437.6 |
| 7,430,946 B2 | * | 10/2008 | Studer | 83/42 |
| 2005/0115373 A1 | * | 6/2005 | Kunkel | 83/168 |

OTHER PUBLICATIONS

Leica Microsystems Nussloch GmbH, "Leica SM2000 R Sliding Microtome—Instruction Manual", Mar. 2004, Nussloch, Germany.

* cited by examiner

*Primary Examiner* — Kenneth E. Peterson
*Assistant Examiner* — Sean Michalski
(74) *Attorney, Agent, or Firm* — Hodgson Russ LLP (57) ABSTRACT

A lever arrangement for a microtome including a first and second lever. The first lever mounted rotatably about a first axis. The second lever is mounted rotatably about a second axis substantially parallel to the first axis. One lever comprises two guidance surfaces. The other lever comprises a guidance segment. The guidance segment coacts with the two guidance surfaces such that a rotation of the first lever in a first direction rotates the second lever in a target direction, and a rotation of the first lever in a direction opposite to the first direction rotates the second lever in the target direction.

17 Claims, 7 Drawing Sheets

MICROTOME HAVING A LEVER ARRANGEMENT

CROSS REFERENCE TO RELATED APPLICATIONS

This application claims priority of German patent application 10 2006 034 879.6 filed Jul. 25, 2006, which is incorporated by reference herein.

FIELD OF THE INVENTION

The present invention relates to a microtome having a lever arrangement. The lever arrangement encompasses a first lever and a second lever. The first lever is mounted rotatably about a first axis and is rotatable by an operator. The second lever is mounted rotatably about a second axis and actuates, for example, an advance mechanism of the microtome.

BACKGROUND OF THE INVENTION

Figure 1:
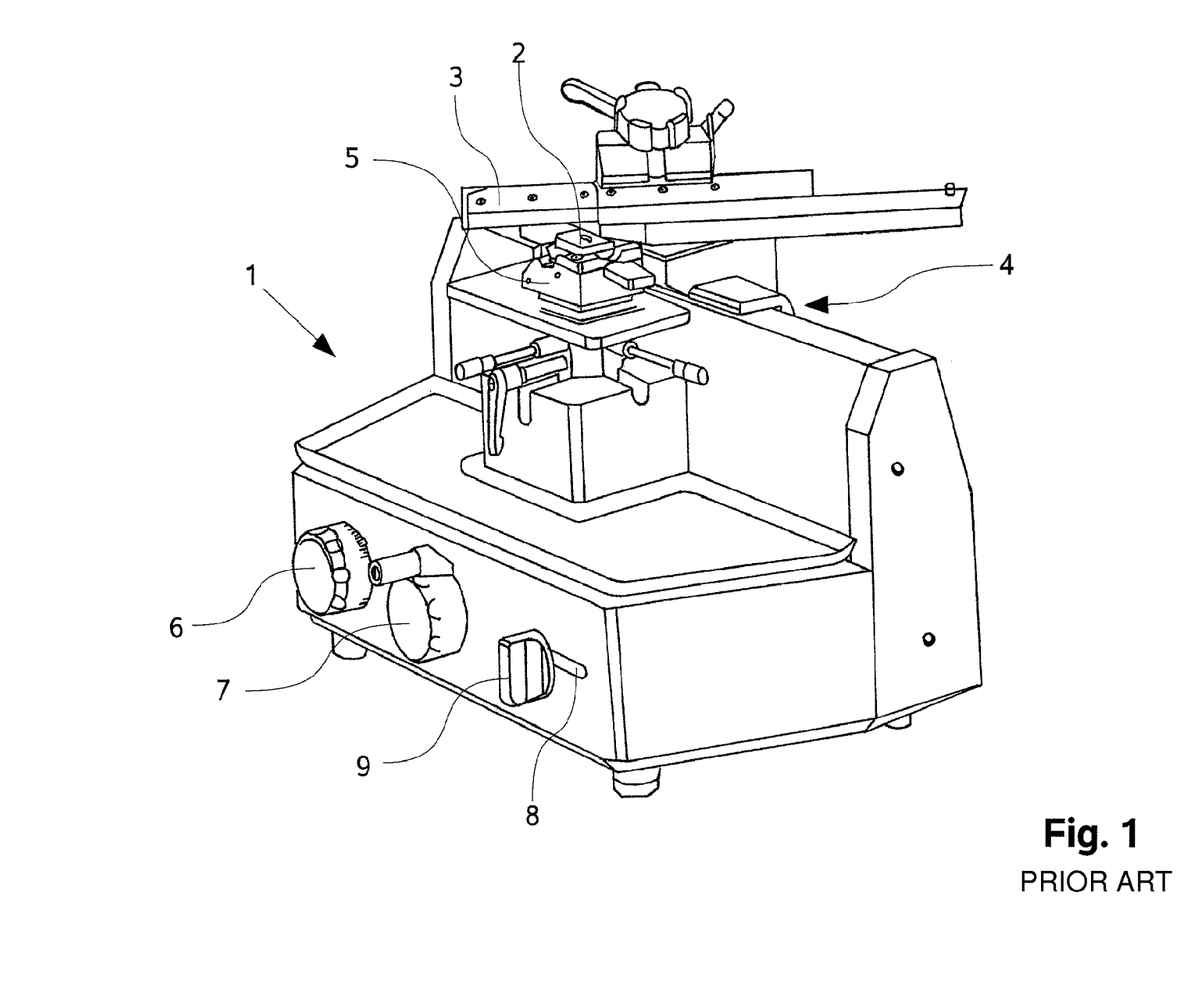
FIG. 1 is a perspective view of a sliding microtome known from the existing art.

The aforesaid lever arrangement for a microtome is used in particular in the context of a sliding microtome of the assignee, namely in the "Leica SM2000 R" model (see also FIG. 1). This sliding microtome is described in printed form in a company brochure of March 2003. In a sliding microtome, the knife that sections the specimen is moved back and forth on a movably arranged slide in order to section the specimen arranged in a specimen holder. The specimen holder is moved vertically onto the knife via a corresponding mechanism, namely a micrometer mechanism; this is also referred to as "advance." The increment with which the specimen is advanced toward the knife can be set to an accuracy of 0.5 μm via a rotary knob fitted with a scale. Provided on the aforementioned sliding microtome as a further operating element is a crank with which a coarse drive mode for specimen movement toward the knife or away from the knife, i.e. substantially in a vertical direction, can be realized. It is possible as a result, after a sample change, to advance the specimen holder along with the specimen rapidly onto the knife, so that the sectioning operations with a definable desired cut thickness can directly follow one another. Provided as a further operating element is a lever (activation lever), guided in an elongated hole and provided with a knob, with which a manual advance motion of the specimen holder toward the knife can be activated. This knob or lever is usually utilized only in the context of advance in sectioning mode, the advance occurring with the increment currently set using the rotary knob fitted with the scale. The lever of this sliding microtome is movable in only one direction, specifically to the right for an operator located in front of the sliding microtome. This sliding microtome also encompasses an operating state with automatic advance, the operating element relevant thereto being arranged on the microtome slide. This automatic advance is usually utilized upon initial cutting of the sample, and replaces actuation of the activation lever.

The activation lever or the lever for manual advance, as well as the advance mechanism coupled thereto, is rotatable in only one direction. It may, however, be desirable to allow an advance of the specimen also to be produced with a rotation of the lever in the opposite direction, for example because different operators are operating a single sliding microtome, and one operator is left-handed and another operator right-handed. Such a requirement at present can be met only by making available two different sliding microtomes, specifically such that with the one sliding microtome a rotation of the lever to the right produces an advance, and with the other sliding microtome a rotation of the lever to the left likewise produces an advance. The rotation direction of the lever is therefore permanently defined in terms of the design.

SUMMARY OF THE INVENTION

It is therefore the object of the present invention to describe and refine a microtome of the kind cited initially with which an advance is possible upon actuation of the lever arrangement in two substantially opposite directions.

The microtome according to the present invention, of the kind cited initially, achieves the aforesaid object. According thereto, a microtome of this kind encompasses a lever arrangement having a first lever and a second lever. The first lever is mounted rotatably about a first axis and is rotatable by an operator. The second lever is mounted rotatably about a second axis and actuates, for example, an advance mechanism of the microtome. The first lever and/or the second lever could also each be mounted pivotably about an axis. The first axis is arranged substantially parallel to the second axis. One of the two levers comprises two guidance surfaces that can be arranged adjacently to one another. The other of the two levers comprises a guidance segment. The guidance segment coacts with the two guidance surfaces in such a way that a rotation of the first lever in a first direction rotates the second lever in a target direction, and a rotation of the first lever in a direction opposite to the first direction likewise rotates the second lever in the target direction.

What has been recognized according to the present invention is firstly that it is not necessary to make available two microtomes that differ in terms of physical design, for example in order to make available for a left-hander a microtome optimally operable by him or her. Instead, a lever arrangement according to the features of Claim 1 is used in the context of a previously existing lever arrangement. For example, the activation lever of the microtome known from the existing art could be replaced by the first and second levers, the two levers being arranged rotatably or pivotably relative to one another. The first lever can thus be rotated in the first direction or in the direction opposite to the first direction, the second lever always being rotated in the same target direction irrespective of the rotation direction of the first lever. The advance mechanism of the microtome, with which the second lever can coact, is thus always actuated in the same fashion, so that ultimately an advance of the specimen takes place.

In a preferred embodiment, the first and/or second lever is embodied in one piece. The first and/or second lever could accordingly comprise an aperture or a pin which defines the rotation axis of the respective lever and with which the respective lever is installed on a housing part of the microtome. The first lever could also comprise an operating element, embodied in one piece with the lever, at which the operator rotates the lever. An operating knob could also be attached on the first lever, which knob is embodied from a different material and is equipped, if applicable, with a resistant coating (because of the operator's hand contact). In this case the first lever is embodied in one piece in terms of its function, but additionally comprises the operating knob.

One of the two levers could comprise a cutout or recess on which the guidance surfaces are provided. The cutout or recess could be embodied in substantially V- or C-shaped fashion. The guidance surfaces could be provided on the inner side of the cutout or recess.

At least one guidance surface could be embodied in substantially planar fashion over at least a subregion, preferably over the entire region. This makes possible simple and accurate manufacture of the first lever, in particular in the context of material-removing production of the first lever. The actuation and transfer characteristics thereby achievable are also favorable for service in a microtome.

In a very particularly preferred embodiment, the two levers, the two axes, the guidance surfaces, and the guidance segment are arranged with respect to one another and embodied in such a way that a part of the guidance segment always comes into engagement against at least one guidance surface. The result is that, firstly, almost backlash-free coaction of the two levers can be achieved. In addition, the second lever is always guided in the context of a rotation motion of the first lever, since a part of the guidance segment always comes into engagement against at least one guidance surface, so that the second lever executes a uniform and smooth rotation motion, which is advantageous in the context of actuation of the microtome's micrometer mechanism.

One of the two levers could be embodied in substantially stepped or step-shaped fashion, and arranged above or below the other lever with a region facing toward the other lever. This applies in particular to a state in which the two levers are installed on the microtome. The arrangement above or below the other lever of the region of the other lever that faces toward the one lever refers in particular to the axes about which the levers can rotate. One part of the one lever thus engages over a part of the other lever, specifically in a mutually facing region of the two levers.

At least one axis about which a roller is rotatably arranged could be provided on the region of the other lever that faces toward the one lever. The roller can be brought into engagement with one of the guidance surfaces. The roller constitutes a part of the guidance segment. The guidance segment preferably comprises two rollers, one roller being engageable with a guidance surface. In particular, a first roller could be engageable with the first guidance surface, and a second roller with the second guidance surface.

Alternatively or additionally, the guidance segment could comprise at least one sliding means or at least one ball that is engageable with at least one guidance surface. This makes possible a rotation or actuation of the second lever, by way of a rotation of the first lever, with little friction.

Because the lever arrangement according to the present invention comprising two levers can replace the one activation lever described above of the microtome known from the existing art, it is advantageous if the first lever, and the region of the second lever that does not overlap with the first lever, are arranged substantially at the same height. "At the same height" refers in this connection to the axes about which the levers are respectively rotatably mounted. The remainder of the advance mechanism of the microtome accordingly can be used in largely unmodified fashion, so that advantageously, a physical modification is to be carried out only at the location of the activation lever of the microtome known from the existing art. In other words, the two levers respectively comprise an upper, lower, and/or lateral surface that are arranged substantially in or close to one plane.

In a preferred embodiment, a means is provided with which the two levers can be forced into a position that corresponds to a middle position of the first lever in terms of the two opposite directions, about which the first lever is rotatable. The first lever is thus positioned in its middle position (in which no advance of the specimen takes place). If the first lever is rotated and the second lever is thereby also rotated, this occurs against the force exerted by the means on the two levers.

In an economical embodiment, the means comprises a spring that engages with its one end on the first lever and with its second end on the second lever. The two ends of the spring engage at suitable points on the two levers in such a way the first lever is thereby forced into its middle position or preloaded in its middle position.

Alternatively thereto, the means could comprise a spring that engages with its one end on a housing part and with its second end on one of the two levers. It is also conceivable for the spring to engage with its one end on a housing part and with its second end on another component joined to the second lever. Such a component could be, for example, a strut of the advance mechanism of the micrometer mechanism. In this case as well, the engagement points of the spring are selected so that the first lever is thereby forced into its middle position.

In a very particularly preferred embodiment the axes of the levers, the guidance surfaces, and the guidance segment are arranged relative to one another and embodied in such a way that, with the two levers in the installed state, a rotation of the first lever in a first direction by or through a predefinable amount or angle results in a rotation of the second lever in the target direction by or through a predefinable amount or angle. The rotation of the first lever in the direction opposite to the first direction by or through the same amount or angle results in a rotation of the second lever in the target direction by or through the same amount or angle. With an arrangement of this kind of the components recited here, the consequence is that the second lever is rotated in the target direction by or through the same amount or angle in each case, irrespective of whether the first lever is rotated by or through a specific amount or angle in the first or in the second direction. The lever arrangement will accordingly actuate the advance mechanism of the micrometer mechanism of the microtome in the same fashion in each case, i.e. irrespective of the rotation direction of the first lever.

In a likewise preferred embodiment the axes of the levers, the guidance surfaces, and the guidance segment are arranged relative to one another and embodied in such a way that, with the two levers in the installed state, a rotation of the first lever by a predefinable amount causes the second lever to be rotated by an amount dependent thereon, a predefinable gearing-down or gearing-up ratio of the rotation of the first lever thereby being possible. In other words, upon a rotation of the first lever of, for example, 10 cm, the second lever is rotated only 5 cm at its end facing toward the advance mechanism of the microtome, so that a gearing-down of the lever travels is thereby present. In comparable fashion, a gearing-up of the lever travels can also be achieved so that, for example, a 5-cm rotation of the first lever rotates the second lever 10 cm. The selection of the gearing ratio ultimately depends on the overall configuration of the advance mechanism of the microtome and on the desired actuation characteristics, which are aimed at ergonomic operation of the microtome.

There are various ways of advantageously embodying and refining the teaching of the present invention. The reader is referred, for that purpose, on the one hand to the claims subordinate to Claim 1, and on the other hand to the explanation below of the preferred exemplifying embodiments of the invention with reference to the drawings. In conjunction with the explanation of the preferred exemplifying embodiments of the invention with reference to the drawings, an explanation is also given of generally preferred embodiments and refinements of the teaching.

DETAILED DESCRIPTION OF THE INVENTION

Identical or similar components or assemblies are labeled with the same reference characters in the Figures.

FIG. 1 shows a sliding microtome 1 of the Applicant, namely the "Leica SM2000 R" model. This sliding microtome is already known from the existing art and does not comprise a lever arrangement according to the present invention. In sliding microtome 1, knife 3 that sections specimen 2 is moved back and forth on a movably arranged slide 4 in order to section specimen 2 arranged in specimen holder 5. Specimen 2 is usually a histological preparation that is embedded in a paraffin block and is clamped into specimen holder 5. Specimen holder 5 is moved vertically onto knife 3 via a corresponding mechanism, namely a micrometer mechanism provided in the housing of sliding microtome 1 and not shown in FIG. 1. The increment with which specimen 2 is advanced upward toward knife 3 can be set, to an accuracy of 0.5 μm, via a rotary knob 6 fitted with a scale. Provided on sliding microtome 1 shown in FIG. 1 as a further operating element is a crank 7 with which a coarse drive mode for movement of the specimen toward knife 3 or away from knife 3 (i.e. substantially in a vertical direction) can be implemented. This makes it possible, after a sample change, to advance specimen holder 5 along with specimen 2 rapidly onto knife 3, so that the sectioning operations at a definable desired cut thickness can directly follow one another. Provided as a further operating element is an activation lever 9, guided in an elongated hole 8, with which a manual advancing motion of specimen holder 5 toward knife 3 can be activated. Activation lever 9 is usually utilized only in the context of advance in sectioning mode; the advance occurs with the increment currently set on rotary knob 6 fitted with the scale. This sliding microtome 1 also encompasses an operating state with automatic advance, the operating element relevant thereto being arranged on microtome slide 4, specifically on the back side (not visible in FIG. 1) of slide 4. This automatic advance is usually utilized upon initial cutting of the sample, and replaces actuation of activation lever 9.

Figure 2:
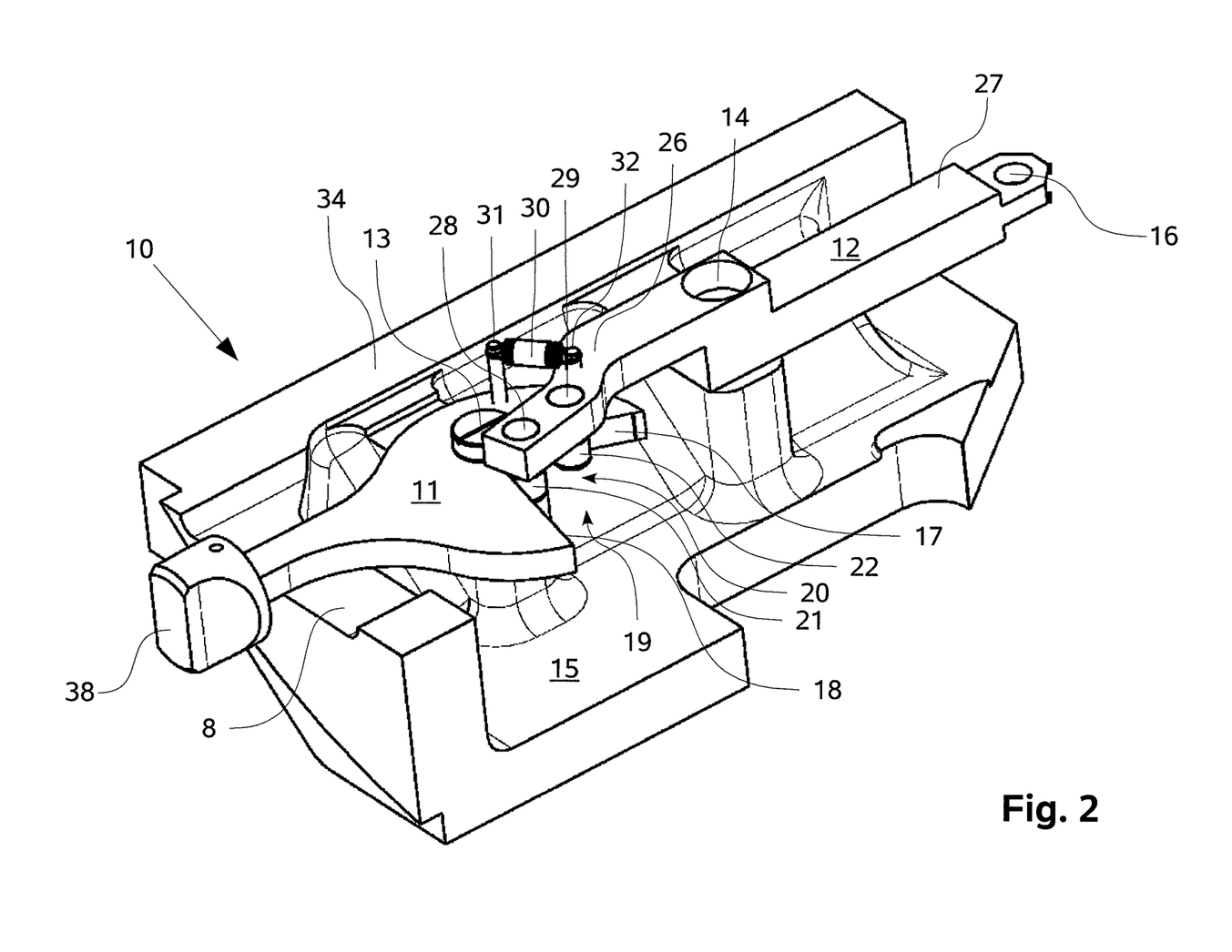
FIGS. 2, 4, and 6 schematically depict, in a perspective view, an exemplifying embodiment of a lever arrangement according to the present invention, in different lever positions in each case.
Figure 3:
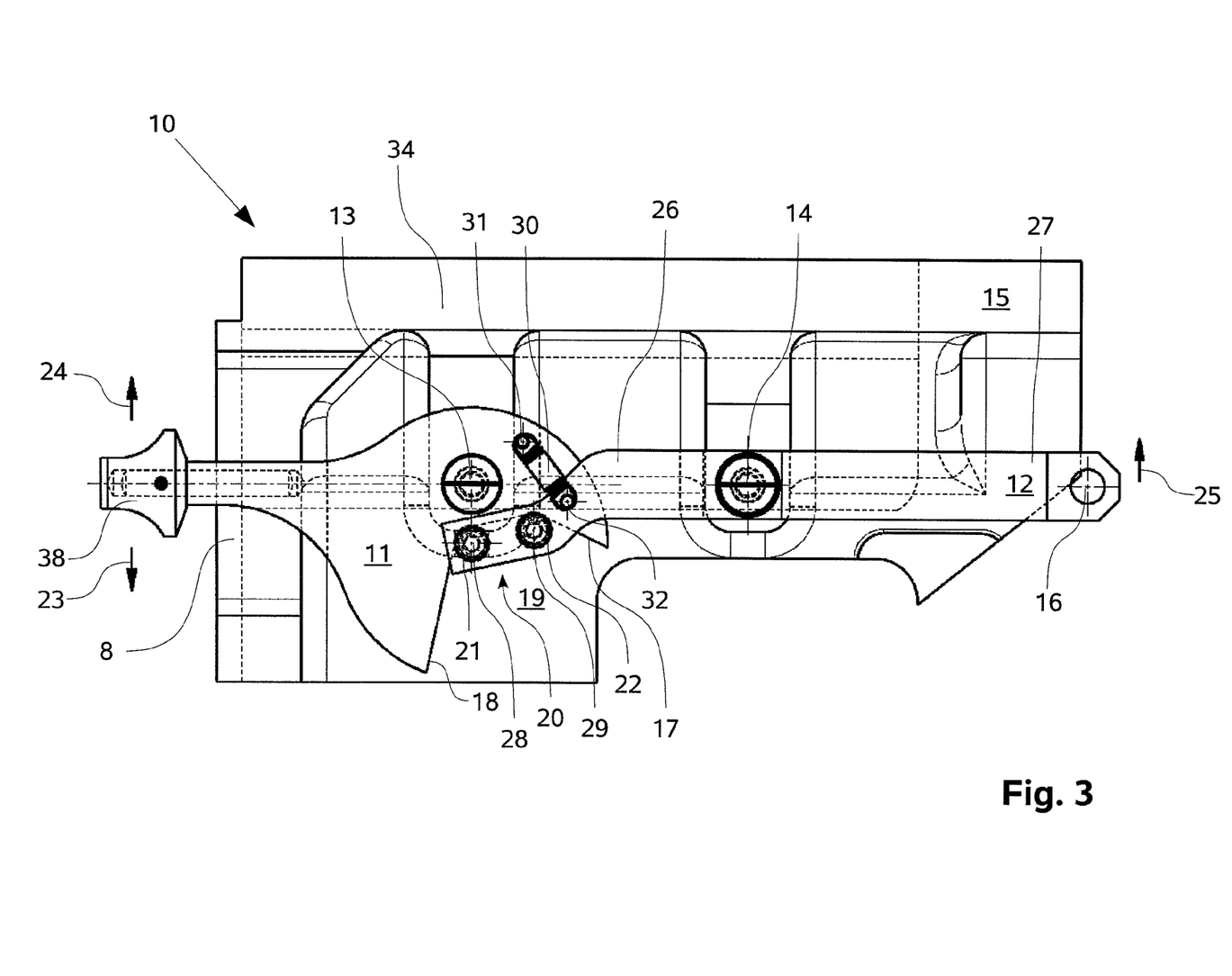
FIGS. 3, 5, and 7 each schematically depict, in a plan view, the exemplifying embodiment of FIGS. 2, 4, and 6 of the lever arrangement according to the present invention, in different lever positions in each case.

FIGS. 2 and 3 show an exemplifying embodiment of lever arrangement 10 according to the present invention that could be used instead of activation lever 9 of sliding microtome 1 of FIG. 1. Lever arrangement 10 of FIGS. 2 and 3 is shown in its middle or centered position. Lever arrangement 10 encompasses a first lever 11 and a second lever 12. First lever 11 is embodied in one piece, and is mounted rotatably about a first axis 13. Second lever 12 is likewise embodied in one piece and is mounted rotatably about a second axis 14. First axis 13 and second axis 14 are oriented parallel to one another, so that the rotation motion of the two levers 11, 12 takes place in a direction perpendicular to the two axes 13, 14. Both first axis 13 and second axis 14 are defined respectively by a screw that is threaded into housing 15. Second lever 12 is joined rotatably/pivotably, with its end 16 that faces away from first lever 11 and has the orifice provided there, to a strut (not shown in the Figure) of an advance mechanism of a microtome.

First lever 11 comprises two guidance surfaces 17, 18 that are constituted in a substantially V- or C-shaped cutout 19 of first lever 11. The two guidance surfaces 17, 18 are each embodied in planar fashion over a large subregion, and enclose an angle of approx. 75 degrees. Second lever 12 comprises a guidance segment 20 that is constituted by two rollers 21, 22. First lever 11 is rotatable in a first direction 23, specifically to the right as depicted in FIG. 2 and downward as depicted in FIG. 3. This rotation direction corresponds to the only possible rotation direction of activation lever 9 of FIG. 1. First lever 11 is also rotatable in a second direction 24, second direction 24 being directed oppositely to first direction 23. First lever 11 can thus also be rotated to the left as depicted in FIG. 2 and upward as depicted in FIG. 3.

Guidance segment 20, and therefore the two rollers 21, 22, of second lever 12 coact with the two guidance surfaces 17, 18 of first lever 11 in such a way that a rotation of first lever 11 in a first direction 23 rotates second lever 12 in a target direction 25. Conversely, a rotation of first lever 11 in a direction 24 opposite to first direction 23 also rotates second lever 12 in target direction 25.

The two levers 11, 12, the arrangement of the two axes 13, 14, guidance surfaces 17, 18, and guidance segment 20 (i.e. the two rollers 21, 22) are arranged with respect to one another and embodied in such a way that a part of guidance segment 21, 22 always comes into engagement against at least one guidance surface 17, 18. In the lever position shown in FIGS. 2 and 3, roller 21 comes into or is in engagement with guidance surface 18, and roller 22 with guidance surface 17.

Figure 4:
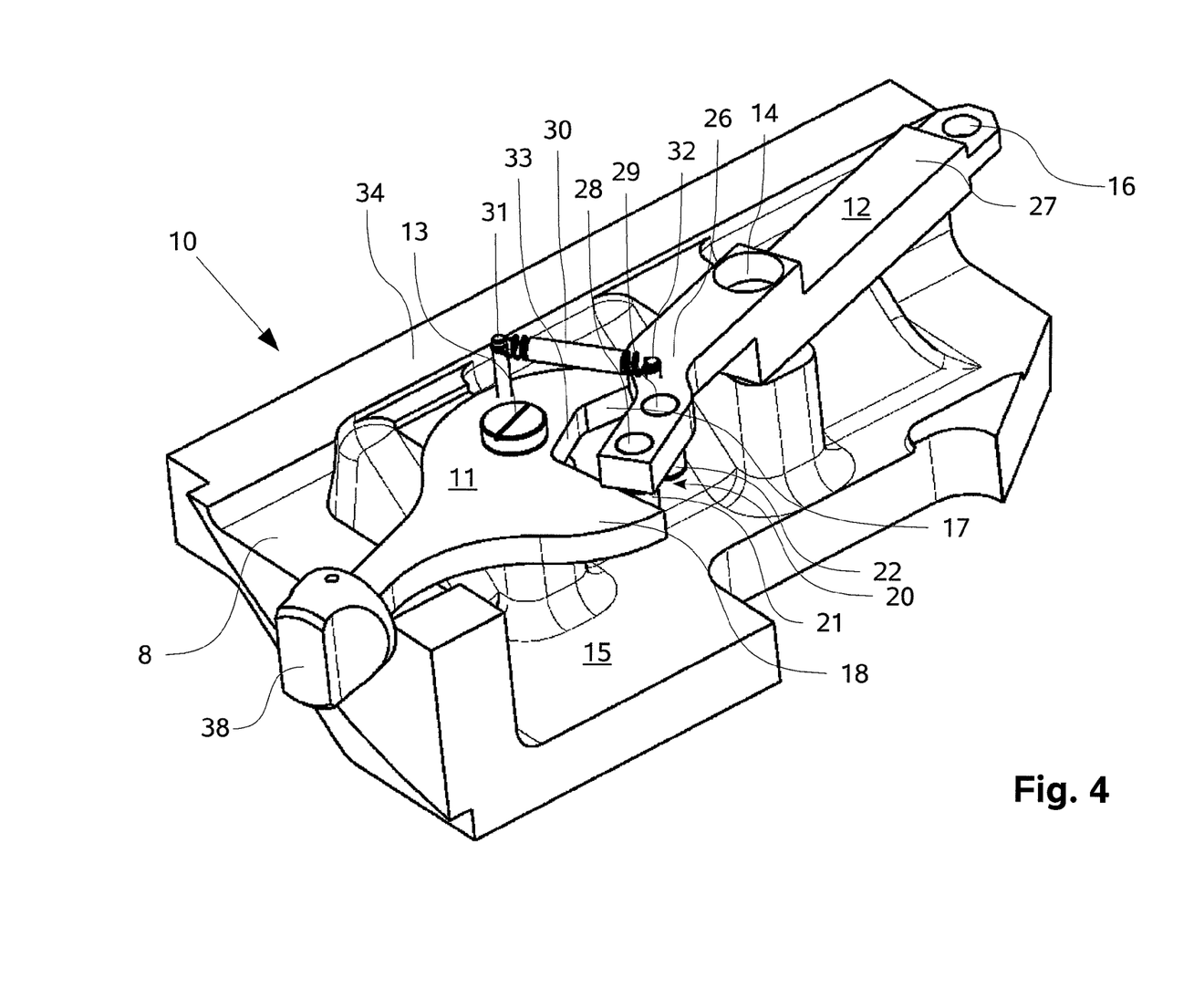
Figure 5:
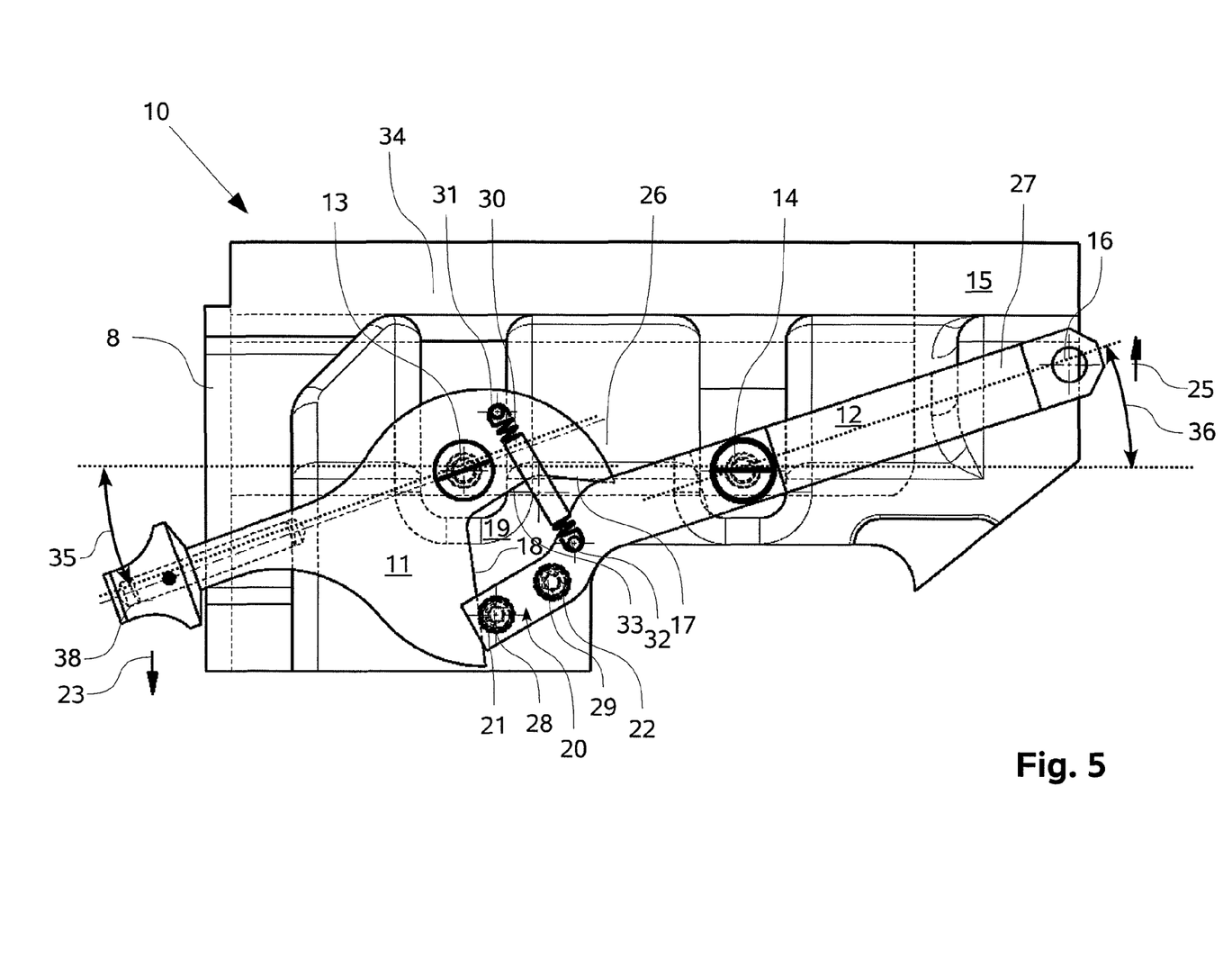
Figure 6:
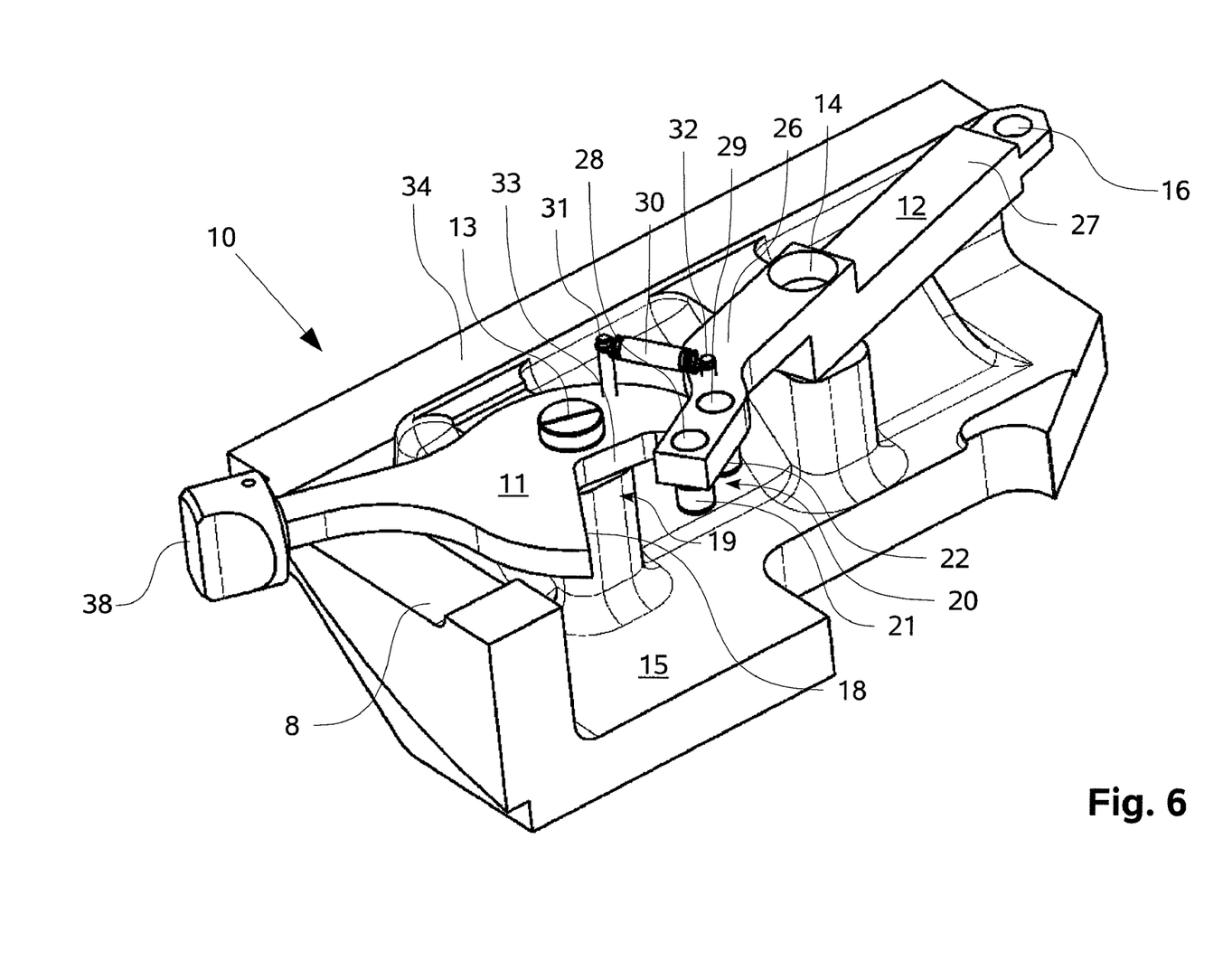
Figure 7:
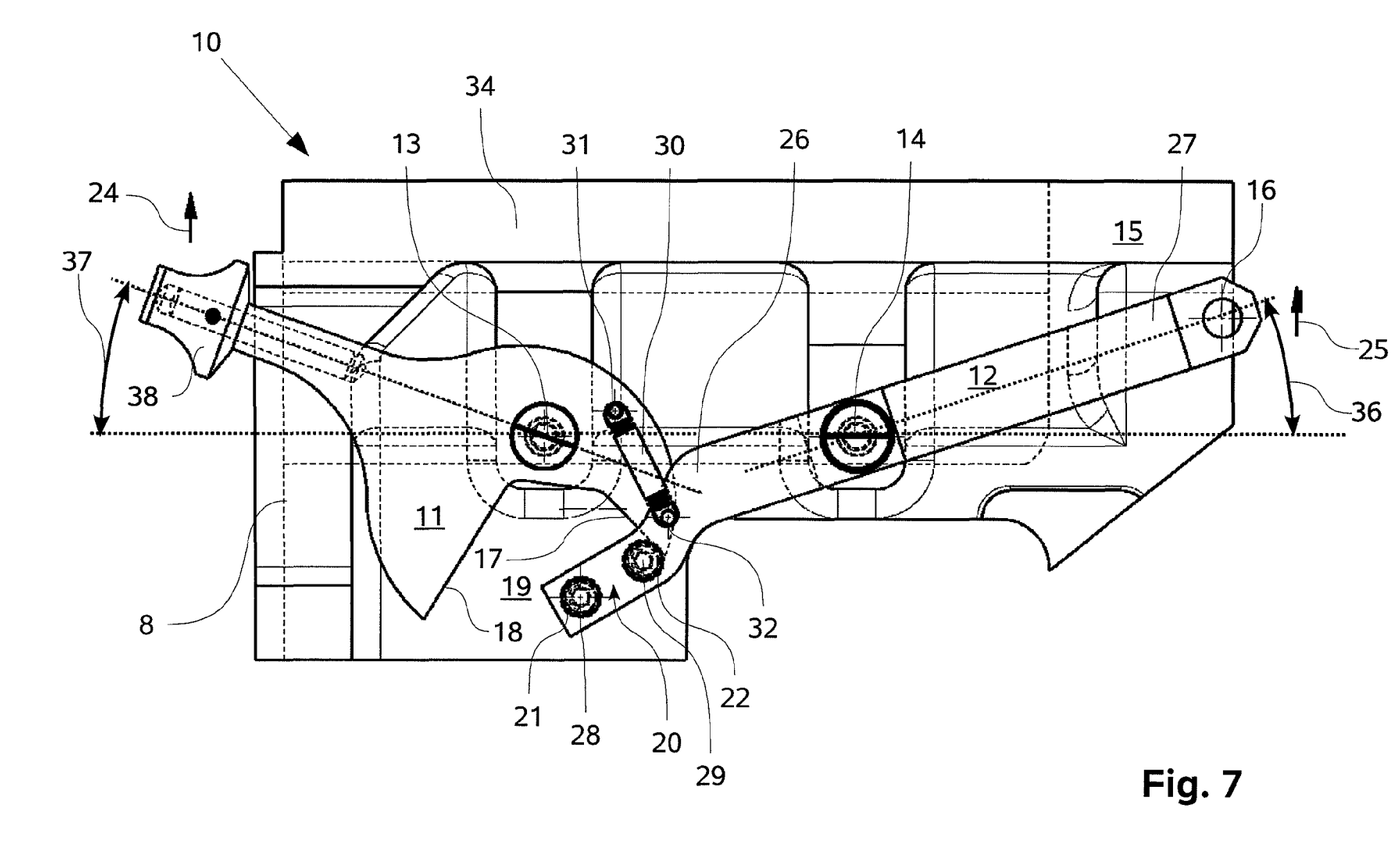

In FIGS. 4 and 5, the exemplifying embodiment according to FIGS. 2 and 3 of lever arrangement 10 according to the present invention is shown in an operating state in which first lever 11 is rotated in first direction 23. It is apparent from what is depicted in FIGS. 4 and 5 that roller 21 comes into engagement with guidance surface 18. In FIGS. 6 and 7, the exemplifying embodiment according to FIGS. 2 and 3 of lever arrangement 10 according to the present invention is shown in an operating state in which first lever 11 is rotated in second direction 24. It is apparent from what is depicted in FIGS. 6 and 7 that roller 22 comes into engagement with guidance surface 17. Roller 21 rolls on guidance surface 18 during the rotation motion of first lever 11 in first direction 23, and is always in contact with guidance surface 18 even during this rolling motion. Roller 22 rolls on guidance surface 17 during the rotation motion of first lever 11 in second direction 24, and is always in contact with guidance surface 17 even during this rolling motion.

Second lever 12 is embodied in stepped fashion. Second lever 12 comprises a first end 26 and a second end 27. First end 26 of second lever 12 is arranged facing first lever 11. Second end 27 of second lever 12 is arranged facing away from first lever 11. As depicted in FIG. 2, second end 26 is embodied above second end 27 of second lever 12. With a region facing toward first lever 11, namely with first end 26, second lever 12 is arranged above first lever 11.

Two axes 28, 29 are provided at first end 26 of second lever 12. Roller 21 is mounted rotatably about axis 28. Roller 22 is mounted rotatably about axis 29.

The downwardly facing surface of first lever 11 and the downwardly facing surface of second end 27 of second lever 12 are, in the state as installed on housing 15, arranged substantially at the same height.

In the exemplifying embodiment according to FIGS. 2 to 7, a spring 30 is provided that is attached, or engages, with its one end on pin 31 and with its other end on pin 32. Pin 31 is arranged on first lever 11, and pin 32 on first end region 26 of second lever 12. Spring 30 is thus arranged and dimensioned in such a way that first lever 11 is forced into a middle position that is shown in FIGS. 2 and 3. In this middle position, the two rollers 21, 22 come into engagement in recess 19 in such a way that roller 21 is arranged in the connecting region of guidance surface 18 and of connecting surface 33 (see, for example, FIG. 6). Connecting surface 33 extends between the two guidance surfaces 17, 18. Roller 22 is arranged in the connecting region of guidance surface 17 and connecting surface 33. When first lever 11 is then rotated in first direction 23 or in second direction 24, this occurs against the spring force of spring 30. This is evident from FIGS. 4 to 7, in which spring 30 is shown in each case in an extended state as compared with FIGS. 3 and 3. Although spring 30 shown in FIGS. 2 to 7 is arranged on the two levers 11, 12 and thus engages on the two levers 11, 12, provision could also be made for a spring to engage or to be attached, for example, with its one end on first end 26 of second lever 12, and with its second end on a region 34 of housing 15; this is not shown in the Figures. This, too, would force second lever 12 and thus also first lever 11 each into their unrotated position.

With levers 11, 12 in the installed state, axes 13, 14 of levers 11, 12, guidance surfaces 17, 18, and guidance segment 20 (or rollers 21, 22) are arranged relative to one another and embodied in such a way that a rotation of first lever 11 in a first direction 23 by a predefinable amount results in a rotation of second lever 12 in target direction 25 by a predefinable amount. The rotation of first lever 11 in a direction 24 opposite to first direction 23 by the same amount results in a rotation of second lever 12 in target direction 25 by the same amount.

The rotation of first lever 11 in first direction 23 by a definable amount is shown in FIGS. 4 and 5 and is indicated in FIG. 5 with double arrow 35. This rotation corresponds to the maximum pivotable angle 35 of first lever 11 about axis 13 in rotation direction 23. A rotation of this kind of first lever 11 through the maximum pivotable angle 35 results in a rotation of second lever 12 in target direction 25 by a definable amount, as indicated in FIG. 5 with double arrow 36. This rotation of second lever 12 corresponds to the maximum pivot range of second lever 12.

The rotation of first lever 11 in second direction 24 by a definable amount is shown in FIGS. 6 and 7 and is indicated in FIG. 7 with double arrow 37. This rotation corresponds to the maximum pivotable angle 37 of first lever 11 about axis 13 in rotation direction 24. A rotation of this kind of first lever 11 through the maximum pivotable angle 37 results in a rotation of second lever 12 in target direction 25 by a definable amount, as indicated in FIG. 7 with double arrow 36. This rotation of second lever 12 shown in FIG. 7 likewise corresponds to the maximum pivot range of second lever 12, as shown in FIG. 5.

Second lever 12 is thus rotated through the same angle 36 in each case, both when first lever 11 is rotated through angle 35 in first direction 23 and when first lever 11 is rotated through angle 37 in second direction 24. Angle 35 and angle 37 of first lever 11 are of equal magnitude.

Axes 13, 14 of levers 11, 12, guidance surfaces 17, 18, and guidance segment 20 are arranged with respect to one another and embodied in such a way that, with the two levers 11, 12 in the installed state, a rotation of first lever 11 by or through a predefinable amount or angle 35, 37 causes second lever 12 to be rotated by or through an amount or angle 36 dependent thereon, a definable gearing-down or gearing-up ratio thereby being possible. In the exemplifying embodiment according to FIGS. 2 to 7, the definable ratio has a value of approximately 1, i.e. a rotation of first lever 11 by or through an amount or angle 35, 37 corresponds substantially to a rotation of second lever 12 by or through the same amount or angle 36.

An operating knob 38 is attached to first lever 11.

In conclusion, be it noted very particularly that the exemplifying embodiments discussed above serve merely to describe the teaching claimed, but do not limit it to the exemplifying embodiments.

PARTS LIST

1 Sliding microtome or microtome
2 Specimen
3 Knife
4 Slide
5 Specimen holder
6 Rotary knob
7 Crank
8 Elongated hole
9 Activation lever for activating manual advance
10 Lever arrangement
11 First lever
12 Second lever
13 First axis of (11)
14 Second axis of (12)
15 Housing
16 End of (12) facing away from first lever (11)
17, 18 Guidance surface of (11)
19 V-shaped cutout of (11)
20 Guidance segment of (12)
21, 22 Roller
23 First direction
24 Second direction, opposite to first direction
25 Target direction of (12)
26 First end of (12)
27 Second end of (12)
28 Axis for (21) on (12)
29 Axis for (22) on (12)
30 Spring between (11) and (12)
31 Pin on (11)
32 Pin on (26, 12)
33 Connecting surface between (17) and (18)
34 Region on (15) on which a spring could be attached
35 Angle upon a rotation of (11) in first direction (23)
36 Angle of a rotation of (12) in target direction (25)
37 Angle upon a rotation of (11) in second direction (24)
38 Operating knob of (11)

What is claimed is:

1. In a microtome having a knife and a specimen holder movable relative to the knife, the improvement comprising:
   a first lever rotatable about a first axis by an operator; and
   a second lever rotatable about a second axis in a target direction, the second axis being substantially parallel to the first axis;
   wherein one of the first and second levers includes two guidance surfaces, and the other of the first and second levers includes a guidance segment, the guidance segment coacting with the two guidance surfaces such that rotation of the first lever in a first direction rotates the second lever in the target direction, and rotation of the first lever in a second direction opposite to the first direction also rotates the second lever in the target direction; and
   wherein at least part of the guidance segment always engages at least one of the two guidance surfaces;
   wherein the guidance segment includes two rollers each rotatable about a respective roller axis for engagement with a respective one of the two guidance surfaces.

2. The microtome improvement according to claim 1, wherein the first lever or the second lever is embodied in one piece.

3. The microtome improvement according to claim 2, wherein an operating knob is attached on the first lever.

4. The microtome improvement according to claim 1, wherein the first lever and the second lever are each embodied in one piece.

5. The microtome according to claim 1, wherein one of the first and second levers includes a cutout defining the two guidance surfaces.

6. The microtome according to claim 5, wherein the cutout is substantially V-shaped or substantially C-shaped.

7. The microtome according to one of claim 1, wherein at least one of the two guidance surfaces is substantially planar over at least a subregion thereof.

8. The microtome according to claim 1, wherein the guidance segment is always in engagement with at least one of the two guidance surfaces.

9. The microtome according to claim 1, wherein one of the first and second levers is stepped, and the first and second levers are arranged to partially overlap one another.

10. The microtome according to claim 9, wherein the guidance segment includes at least one ball for engagement with at least one of the two guidance surfaces.

11. The microtome according to claim 9, wherein the guidance segment includes at least one slider for engagement with at least one of the two guidance surfaces.

12. The microtome according to claim 1, wherein the first lever, and a region of the second lever that does not overlap with the first lever, are arranged substantially at the same height.

13. The microtome according to claim 1, wherein the first lever is rotatable about the first axis in opposite rotational directions, and the microtome further comprises a spring arranged to urge the first and second levers toward a middle position with respect to rotation of the first lever in opposite rotational directions.

14. The microtome according to claim 13, wherein one end of the spring is attached to the first lever and another end of the spring is attached to the second lever.

15. The microtome according to claim 13, wherein the microtome further includes a housing on which the first and second levers are mounted, and one end of the spring is attached to the housing and another end of the spring is connected to one of the first and second levers.

16. The microtome improvement according to claim 1, wherein a rotation of the first lever in a first direction by a predefined input amount results in a rotation of the second lever in the target direction by a predefined output amount, and a rotation of the first lever in a direction opposite to the first direction by the same input amount results in a rotation of the second lever in the target direction by the same output amount.

17. The microtome according to claim 1, wherein a rotation of the first lever by a predefined input amount causes the second lever to rotate by an output amount proportional to the input amount by a predefined gearing-down or gearing-up ratio.

* * * * *